United States Patent [19]

Clovis et al.

[11] 4,001,176

[45] Jan. 4, 1977

[54] RING PHOSPHONATES AS FLAME-RETARDANTS

[75] Inventors: James S. Clovis; Francis R. Sullivan, both of Warminster, Pa.

[73] Assignee: Rohm and Haas Company, Philadelphia, Pa.

[22] Filed: Apr. 26, 1973

[21] Appl. No.: 354,730

Related U.S. Application Data

[62] Division of Ser. No. 139,949, May 3, 1971, Pat. No. 3,812,219.

[52] U.S. Cl. ............................... 260/45.8 R
[51] Int. Cl.² ............................... C08K 5/53
[58] Field of Search ............................ 260/45.8

[56] References Cited
UNITED STATES PATENTS

| | | | |
|---|---|---|---|
| 2,944,526 | 7/1960 | Atherton | 260/936 |
| 3,305,526 | 2/1967 | Cuttag | 260/45.8 R |

*Primary Examiner*—V. P. Hoke
*Attorney, Agent, or Firm*—Lester E. Johnson

[57] ABSTRACT

A nine-membered ring phosphonate compound having the formula

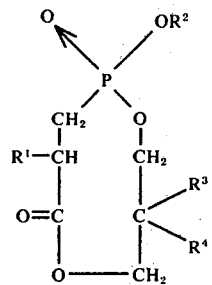

wherein $R^1$ is hydrogen or methyl, $R^2$ is phenyl or substituted phenyl wherein the substitution is one or more of halogen, nitro, lower alkyl, cyclohexyl, alkoxy, naphthoxy or phenoxy and $R^3$ and $R^4$ are the same or different and are lower alkyl of up to eight carbon atoms, preferably methyl, is formed by the reaction of acrylic or methacrylic acid with a compound of the general formula

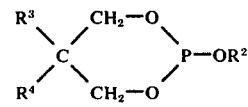

wherein $R^2$, $R^3$ and $R^4$ are as above. The ring phosphonates are useful for forming flame-retardant compositions from mixtures comprising the phosphonate and methyl methacrylate.

6 Claims, No Drawings

RING PHOSPHONATES AS FLAME-RETARDANTS

This is a division, of application Ser. No. 139,949, filed May 3, 1971 now U.S. Pat. No. 3,812,219.

The present invention relates to novel nine-membered ring phosphonate compounds, to a process for making these compounds and to acrylic compositions of superior flame-resistant properties. The acrylic compositions comprise an addition polymer formed from a mixture containing the novel phosphonate compounds.

The reaction of phosphites with unsaturated acids and esters is generally known. Drawing analogy from this prior art as exemplified by *Topics in Phosphorus Chemistry*, vol. 1, Interscience (1964), pp. 92–94 and *Structure and Mechanism in Organo-Phosphorus Chemistry*, Hudson, Academic Press (1965), pp. 192–196, it might be predicted that the reaction between a cyclic phosphite and an $\alpha$-$\beta$-unsaturated acid such as acrylic or methacrylic would produce a polymeric product.

It has surprisingly been found in the present invention that a nine-membered phosphonate compound of the general formula

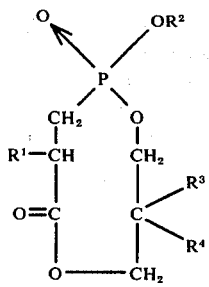

wherein $R^1$ is hydrogen or methyl, $R^2$ is phenyl or substituted phenyl wherein the substitution is one or more of halogen, nitro, lower alkyl, cyclohexyl, alkoxy, naphthoxy or phenoxy and $R^3$ and $R^4$ are the same or different and are lower alkyl of up to eight carbon atoms, preferably methyl, is formed by the reaction of acrylic or methacrylic acid with a cyclic phosphite of the general formula

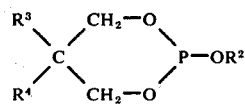

wherein $R^2$, $R^3$ and $R^4$ are as above. It has been found that these novel ring phosphonate compounds are useful for forming flame resistant compositions from monomer mixtures comprising the phosphonate and methyl methacrylate.

It is particularly notable that the phosphonate compositions of the present invention exhibit excellent thermal stability. This property is of particular importance where the compositions are to be incorporated into molding powders for processing by extrusion and molding operations. Commonly used commercial flame-retardant phosphonate compositions such as that prepared from ethylene chlorophosphite and acetone and that prepared from acetaldehyde, ethylene oxide and $PCl_3$ are not stable above about 180° C. while common processing temperatures for molding powders are near 250° to 275° C. The phosphonate compositions of the present invention are advantageously thermally stable at these processing temperatures.

The cyclic phosphite used to prepare the products of the present invention may be prepared according to the procedure set out in Hechenbleikner et al., U.S. Pat. No. 2,834,798, issued May 13, 1958. In the general formula given above for these phosphites it is preferred that $R^2$ be phenyl and $R^3$ and $R^4$ both be methyl so that the preferred nine-membered ring phosphonate compounds of this invention are 2-oxo-2-phenoxy-5-oxo-8,8 dimethyl(1,6-dioxa-2-phosphacyclononane) and 2-oxo-2-phenoxy-4-methyl-5-oxo-8,8-dimethyl-(1,6-dioxa-2-phosphacyclononane).

The acrylic compositions of the present invention may be, for example, an acrylic sheet material or an acrylic molding composition. The acrylic compositions of the present invention comprise an addition polymer formed from a mixture comprising; (a) at least 50 percent by weight of methyl methacrylate, and (b) 5 to 30 percent by weight of a flame-retardant nine-membered ring phosphonate defined by the general formula given supra. The mixture may additionally comprise 10 to 20 weight percent of a member selected from the class consisting of isobornyl acrylate, isobornyl methacrylate and mixtures thereof and/or up to 25 weight percent of an ethylenically unsaturated acrylic compound such as acrylic or methacrylic acid.

The acrylic composition of this invention may be formed by any process known in the art such as for example those referred to and shown in Forsyth, U.S. Pat. Application, Ser. No. 819,484, filed Apr. 25, 1969 now U.S. Pat. No. 3,634,554 granted Jan. 11, 1972.

The addition polymer may constitute the entire body of the composition or it may, for example, constitute the main body and serve as a binder in sheet form for common additives such as coloring dyes or pigments, release agents and other additives.

A preferred embodiment of this invention is an acrylic composition, the main body of which is an addition polymer formed from a mixture comprising (a) 50 to 70 weight percent methyl methacrylate, (b) 15 to 25 weight percent of the flame-retardant, and (c) 10 to 20 weight percent isobornyl acrylate, isobornyl methacrylate or mixtures thereof. Another embodiment of this invention is an acrylic sheet, the main body of which is an addition polymer formed from a mixture comprising (a) at least 50 weight percent of methyl methacrylate, (b) 10 to 30 weight percent of the flame-retardant, and (c) 0.5 to 25 weight percent acrylic or methacrylic acid.

The ethylenically unsaturated acrylic monomer, which may be used in quantities up to 25 weight percent includes monoethylenically unsaturated acrylic compounds and polyethylenically unsaturated acrylic compounds. These unsaturated acrylic compounds constitute a class of compounds known in the art and include but are not limited to such compounds a methacrylic acid, acrylic acid, alkyl esters and substituted alkyl esters of acrylic acid and methacrylic acids, such as ethyl acrylate, butyl acrylate, 2-ethylhexyl acrylate, isobutyl acrylate, isobutyl methacrylate, ethyl-thioethyl methacrylate or acrylate, isobutyl acrylate, halogenated alkyl methacrylate, glycidyl methacrylate and the like; and di- or polyacrylic esters of diols and polyols, such as 1,3-butylene dimethacrylate, 1,3-butylene diacrylate, trimethylolpropane trimethacrylate and the like; acrylic nitriles, such as acrylonitrile, methacrylonitrile and the like. The inclusion of these ethylenically unsaturated acrylic compounds offers special characteristics that are particularly useful in some enduse applications. For example, the inclusion of methacrylic acid improves physical properties including the heat distortion temperature and clarity when some polymeric phosphorus compounds are utilized in the invention. The preferred amount of methacrylic acid is 0.5 to 5%. Polyethylenically unsaturated acrylic monomers or acrylic esters may be utilized to improve high temperature heat resistance and other physical properties. Generally, the concentrations of the polyethylenically unsaturated monomers are maintained at a low level to allow thermoforming of the sheet or injection molding of molding powders. The ethylenically unsaturated acrylic monomers may be a mixture of two or more of the compounds from the class.

To assist those skilled in the art in the practice of the present invention, the following modes of operation are set forth as illustrations, parts and percentages being by weight unless otherwise specifically noted.

EXAMPLE 1

This example illustrates the preparation of a cyclic phosphite useful for preparing the nine-membered ring phosphonate compounds of the present invention.

One mole of 2,2-dimethyl-1,3-propanediol (neopentyl glycol) and one mole of triphenyl phosphite are mixed in a flask. The mixture is heated gradually on an oil bath at 10 to 15 mm pressure; phenol distilling off through a small column. The product, 2-phenoxy-5,5-dimethyl-1,2,3-dioxaphosphorirane, having a $\eta_D^{250}$ of 1.50375 is recovered by distillation at 90°–95° C. at 1.

EXAMPLE 2

This example illustrates the preparation of the nine-membered ring phosphonate compounds of the present invention.

A solution of 22.6 g. (0.1 mole) of the 2-phenoxy-5,5-dimethyl-1,2,3-dioxaphosphorirane of Example 1 and 7.2 g. (0.1) mole of acrylic acid (both freshly distilled) are dissolved in 29.8 g. of reagent grade ethylene dichloride. The solution is degassed and blanketed with nitrogen. The solution temperature is maintained below 25° C. for about seven hours. After 22 hours, the light yellow solution is concentrated and added to a 2:1 solution of ether:CCl$_4$ to give 15.8 g. of product, m.p. 93°–95° C. yield 53%. Carefully purified product has a melting point of 96.9° C.

A sample of the product is characterized by mass spectroscopy, infra-red, nuclear magnetic resonance, elemental analysis and molecular weight. The mass number is 298 and a molecular weight of 327 is obtained. The elemental analysis is in agreement with a 1 to 1 adduct. All of the data are in agreement with a nine-membered ring phosphonate of the structure;

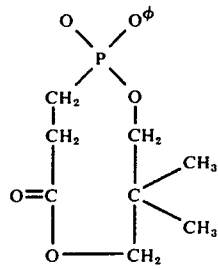

wherein $\phi$ is phenyl. This compound is designated OPOD (DPCN) as an abbreviation for 2-oxo-2-phenoxy-5-oxo-8,8-dimethyl-(1,6-dioxa-2-phosphacyclononane).

EXAMPLES 3 to 9

This example illustrates the preparation of acrylic sheet material of the present invention.

A solution of 25 percent acetyl peroxide in dimethyl phthalate is added to metyl methacrylate (MMA) to give a 0.03 percent concentration of the peroxide and methacrylate. The mixture is combined with the cyclic phosphonate, OPOD(DPCN), prepared in Example 1 in a ratio of 12.5 parts phosphonate and 87.5 parts MMA and with additives such as chain regulators, color dyes, lubricants and the like. The resulting mixture is cured between glass plates. The cured cast sheets, 0.120 to 0.130 inches thick are removed. Samples of the cast sheets are flame tested by ASTM D 635-56T. The cast sheet burns at a rate of 0.8 inches/minute.

The compositions indicated in the Table are prepared according to the preceding procedure and are tested for flame advance, ASTM D 635-56 T, with the results as indicated. The following abbreviations are used; methyl methacrylate (MMA); the nine-membered ring phosphonate of Example 2 [OPOD(DPCN)], isobornyl methacrylate (IBOMA), and tertiary-butyl methacrylate (t-BMA).

Table

| Example | Composition | Burning Rate (Inches/minute) |
|---|---|---|
| 3 | OPOD(DPCN)/MMA; 12.5/87.5 | 0.8 |
| 4 | MMA; 100 percent | 1.3 |
| 5 | IBOMA/MMA; 15/85 | 1.0 |
| 6 | IBOMA/MMA; 30/70 | 1.3 |
| 7 | OPOD(DPCN)/MMA/IBOMA; 20/68/12 | 0.3 |
| 8 | OPOD(DPCN)/MMA/t-BMA; 20/68/12 | 0.5 |
| 9 | OPOD(DPCN)/MMA; 20/80 | 0.6 |

EXAMPLE 10

Two samples prepared from 2-phenoxy-5,5-dimethyl-1,2,3-dioxaphosphorirane and methacrylic acid are prepared by the procedures of Example 2. The first sample exhibits an acid number of 38 which rises to 40 after 2 ½ days at 180° C.; the second sample exhibits an acid number of 20 which rises to 36 after the same length of time at the same temperature. A commercial flame-retardant prepared from ethylene chlorophosphite and acetone shows an acid number of about 6 which after 2 ½ days at 180° C. rises to 300 and a product of acetaldehyde, ethylene oxide and PCl$_3$ shows a first acid number of 6 and after the same treatment exhibits a number of about 130. This example shows the improved thermal stability of the products of the present invention compared to other known flame-resistant compositions.

What is claimed is:

1. As an article of manufacture, an acrylic composition comprising an addition polymer formed from a mixture comprising:
   a. at least 50 percent by weight of methyl methacrylate; and b. 5 to 30 percent by weight of a flame-resistant phosphorus compound defined by the general formula:

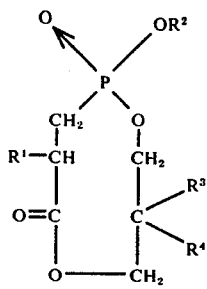

wherein R¹ is selected from the group consisting of hydrogen and methyl, R² is phenyl or substituted phenyl wherein the substitution is one or more of halogen, nitro, lower alkyl, cyclohexyl, alkoxy, naphthoxy, or phenoxy, and R³ and R⁴ are the same or different and are lower alkyl of up to 8 carbon atoms.

2. The acrylic composition of claim 1 wherein the polymer is formed from a mixture additionally comprising a member selected from the group consisting of isobornyl acrylate, isobornyl methacrylate and mixtures thereof.

3. The acrylic composition of claim 1 wherein the polymer is formed from a mixture additionally comprising an ethylenically unsaturated acrylic compound.

4. The acrylic composition of Claim 1 wherein the polymer is formed from a mixture additionally comprising acrylic or methacrylic acid.

5. As an article of manufacture, an acrylic composition comprising an addition polymer formed from a mixture comprising:
   a. at least 50 percent by weight of methyl methacrylate; and
   b. 5 to 30 percent by weight of a flame-resistant phosphorus compound defined by the general formula (b) of Claim 1 wherein R¹ is hydrogen, R² is phenyl, and R³ and R⁴ are methyl.

6. As an article of manufacture, an acrylic composition comprising an addition polymer formed from a mixture comprising:
   a. at least 50 percent by weight of methyl methacrylate; and
   b. 5 to 30 percent by weight of a flame-resistant phosphorus compound defined by the general formula (b) of Claim 1 wherein R¹ is methyl, R² is phenyl, and R³ and R⁴ are methyl.

* * * * *